United States Patent
Nagata et al.

(10) Patent No.: US 11,992,367 B2
(45) Date of Patent: May 28, 2024

(54) ACOUSTIC-WAVE-PROBE RESIN MATERIAL, ACOUSTIC LENS, ACOUSTIC WAVE PROBE, ACOUSTIC WAVE DETERMINATION DEVICE, ULTRASOUND DIAGNOSTIC APPARATUS, PHOTO-ACOUSTIC WAVE DETERMINATION DEVICE, ULTRASONIC ENDOSCOPE, AND METHOD FOR PRODUCING ACOUSTIC LENS

(71) Applicant: FUJIFILM Corporation, Tokyo (JP)

(72) Inventors: Yuzo Nagata, Kanagawa (JP);
Yoshihiro Nakai, Kanagawa (JP);
Shigeki Uehira, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 973 days.

(21) Appl. No.: 16/941,678

(22) Filed: Jul. 29, 2020

(65) Prior Publication Data
US 2020/0352449 A1  Nov. 12, 2020

Related U.S. Application Data

(63) Continuation of application No. PCT/JP2019/010883, filed on Mar. 15, 2019.

(30) Foreign Application Priority Data

Mar. 26, 2018  (JP) ................................. 2018-058355

(51) Int. Cl.
| | |
|---|---|
| A61B 8/00 | (2006.01) |
| A61B 5/00 | (2006.01) |
| C08F 212/08 | (2006.01) |
| C08F 230/08 | (2006.01) |
| C08F 283/12 | (2006.01) |
| C08F 290/06 | (2006.01) |
| C08G 18/61 | (2006.01) |
| G10K 11/30 | (2006.01) |
| H04R 17/00 | (2006.01) |

(52) U.S. Cl.
CPC .......... *A61B 8/4281* (2013.01); *A61B 5/0095* (2013.01); *A61B 8/4444* (2013.01); *A61B 8/445* (2013.01); *C08F 212/08* (2013.01); *C08F 283/12* (2013.01); *C08F 290/068* (2013.01); *C08G 18/61* (2013.01); *G10K 11/30* (2013.01); *C08F 230/08* (2013.01); *H04R 17/005* (2013.01)

(58) Field of Classification Search
CPC .... C08F 220/22; C08F 220/24; C08F 218/20; C08F 218/22; C08F 214/18; C08F 214/182; C08F 214/184; C08F 214/188
See application file for complete search history.

(56) References Cited

U.S. PATENT DOCUMENTS

| | | | | |
|---|---|---|---|---|
| 5,079,312 A | * | 1/1992 | Isozaki .................. | C08G 77/20 526/279 |
| 2005/0240102 A1 | | 10/2005 | Rachlin et al. | |
| 2010/0256496 A1 | | 10/2010 | Zhu | |
| 2011/0306713 A1 | * | 12/2011 | Ueda ..................... | C08F 220/24 524/265 |
| 2017/0009072 A1 | | 1/2017 | Kobayashi et al. | |
| 2019/0023831 A1 | | 1/2019 | Nagata et al. | |
| 2019/0218394 A1 | | 7/2019 | Nagata et al. | |

FOREIGN PATENT DOCUMENTS

| | | |
|---|---|---|
| JP | 62-89765 A | 4/1987 |
| JP | 2005-532871 A | 11/2005 |
| WO | 2015/159603 A1 | 10/2015 |
| WO | 2017/170215 A1 | 10/2017 |
| WO | 2018/061991 A1 | 4/2018 |

OTHER PUBLICATIONS

Extended European Search Report dated Apr. 29, 2021 in European Application No. 19774623.3.
International Search Report dated May 21, 2019, issued by the International Searching Authority in application No. PCT/JP2019/010883.
Written Opinion dated May 21, 2019, issued by the International Searching Authority in application No. PCT/JP2019/010883.
International Preliminary Report on Patentability dated Sep. 29, 2020 together with a translation of the Written Opinion, issued by the International Bureau in application No. PCT/JP2019/010883.

* cited by examiner

*Primary Examiner* — Christopher M Rodd
(74) *Attorney, Agent, or Firm* — Sughrue Mion, PLLC

(57) ABSTRACT

Provided are a resin material that provides a resin shaped article (such as a resin sheet) having an acoustic impedance close to that of a living body, a reduced acoustic wave attenuation even at high frequencies (such as 10 MHz), and high hardness and high tear strength, and that is suitable as a lens material for acoustic wave probes; an acoustic lens, an acoustic wave probe, an acoustic wave determination device, an ultrasound diagnostic apparatus, a photo-acoustic wave determination device, and an ultrasonic endoscope that employ the above-described resin material as a constituent material; and a method for producing the above-described acoustic lens.

11 Claims, 1 Drawing Sheet

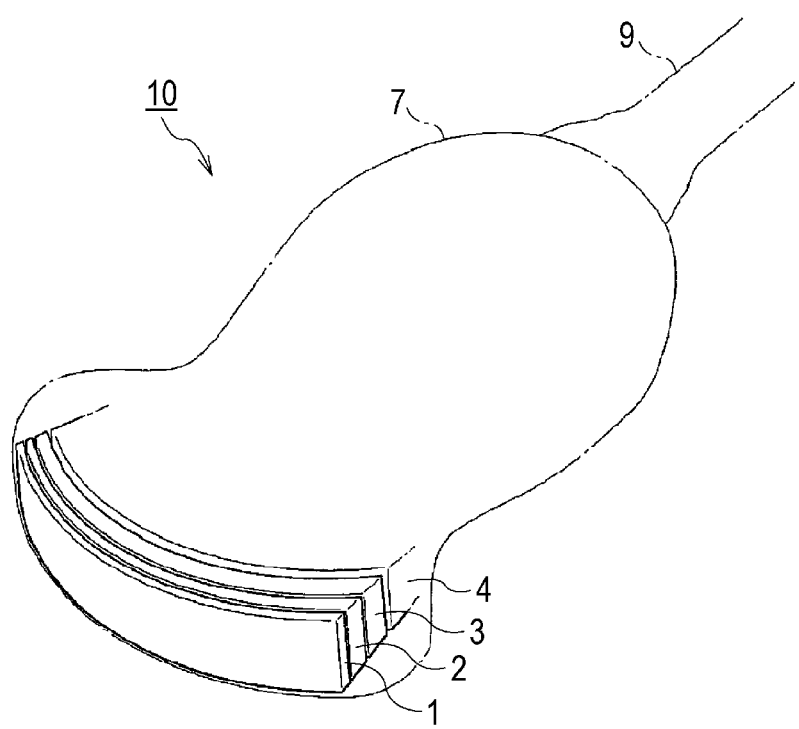

ACOUSTIC-WAVE-PROBE RESIN MATERIAL, ACOUSTIC LENS, ACOUSTIC WAVE PROBE, ACOUSTIC WAVE DETERMINATION DEVICE, ULTRASOUND DIAGNOSTIC APPARATUS, PHOTO-ACOUSTIC WAVE DETERMINATION DEVICE, ULTRASONIC ENDOSCOPE, AND METHOD FOR PRODUCING ACOUSTIC LENS

CROSS-REFERENCE TO RELATED APPLICATIONS

This application is a Continuation of PCT International Application No. PCT/JP2019/010883 filed on Mar. 15, 2019, which claims priority under 35 U.S.C. § 119 (a) to Japanese Patent Application No. 2018-058355 filed in Japan on Mar. 26, 2018. Each of the above applications is hereby expressly incorporated by reference, in its entirety, into the present application.

BACKGROUND OF THE INVENTION

1. Field of the Invention

The present invention relates to an acoustic-wave-probe resin material, an acoustic lens, an acoustic wave probe, an acoustic wave determination device, an ultrasound diagnostic apparatus, a photo-acoustic wave determination device, an ultrasonic endoscope, and a method for producing an acoustic lens.

2. Description of the Related Art

Acoustic wave determination devices use an acoustic wave probe that irradiates a determination target or portion (hereafter, also simply referred to as a target) with acoustic waves, receives the resultant reflected waves (echoes), and outputs signals. Electrical signals converted from the reflected waves received by the acoustic wave probe are displayed as an image. Thus, the inside of the determination target is visualized and observed.

As acoustic waves, for example, ultrasonic waves or photo-acoustic waves having an appropriate frequency are selected in accordance with, for example, the determination target and/or determination conditions.

For example, ultrasound diagnostic apparatuses transmit ultrasonic waves to the inside of a determination target, receive ultrasonic waves reflected by the tissue in the inside of the determination target, and display the ultrasonic waves as an image. Photo-acoustic wave determination devices receive acoustic waves emitted from the inside of the determination target due to the photo-acoustic effect, and display the acoustic waves as an image. The photo-acoustic effect is a phenomenon in which, upon irradiation of a determination target with electromagnetic pulses such as visible light, near-infrared light, or microwaves, the determination target absorbs the electromagnetic waves to generate heat and thermally expand, to thereby generate acoustic waves (typically, ultrasonic waves).

The acoustic wave determination devices transmit acoustic waves to and receive acoustic waves from a living body serving as a determination target, and hence are required to satisfy requirements such as matching of acoustic impedance relative to a living body (typically, the human body) and a reduction in the attenuation of acoustic waves.

For example, one of acoustic wave probes, an ultrasound-diagnostic-apparatus probe (also referred to as an ultrasonic wave probe) includes a piezoelectric element that transmits and receives ultrasonic waves and an acoustic lens, which is a part brought into contact with a living body. The ultrasonic waves emitted from the piezoelectric element pass through the acoustic lens and enter the living body. When there is a large difference between the acoustic impedance (density× acoustic velocity) of the acoustic lens and the acoustic impedance of the living body, the ultrasonic waves are reflected by the surface of the living body, so that the ultrasonic waves do not efficiently enter the living body. For this reason, it is difficult to achieve high resolution. In addition, in order to transmit and receive ultrasonic waves at high sensitivity, the acoustic lens desirably has a low ultrasonic wave attenuation. Furthermore, the acoustic wave probe is required to have, in addition to the above-described acoustic characteristics, sufficient mechanical strength. Specifically, since the acoustic wave probe is used so as to be rubbed over, or sometimes pressed to, a living body, the mechanical strength (such as hardness and tear strength) of the acoustic lens directly affects the service life of the acoustic wave probe.

Silicone resin or rubber (hereafter, silicone resin and rubber may also be collectively referred to as "silicone resin etc.") has an acoustic impedance close to that of a living body (in the case of the human body, 1.40 to $1.70 \times 10^6$ $kg/m^2/sec$) and has a low ultrasonic wave attenuation, and hence has been used as one of the materials for acoustic lenses. This silicone resin etc. can be prepared so as to include mineral filler (also referred to as inorganic filler), to thereby increase the specific gravity of the silicone resin etc., to make the acoustic impedance of the silicone resin etc. be closer to that of a living body. However, in order to try to achieve the required acoustic impedance, the amount of mineral filler added to the silicone resin etc. inevitably increases. As a result, ultrasonic waves are scattered and the acoustic wave attenuation increases, which is problematic.

As a technique for addressing this problem, for example, JP1987-89765A (JP-S62-89765A) describes a silicone rubber composition containing an organopolysiloxane containing a halogen-substituted alkyl group. JP1987-89765A (JP-S62-89765A) states that, in the case of using the silicone rubber composition, use of mineral filler in an amount smaller than in the existing silicone rubber compositions using dimethylpolysiloxane provides a sheet that has an acoustic impedance close to that of a living body and that has a reduced acoustic wave attenuation. On the other hand, WO2017/170215A describes an acoustic-wave-probe resin composition containing a polymer having a structure unit having a siloxane bond and a structure unit having a urea bond. WO2017/170215A states that, without the use of mineral filler, a resin sheet can be obtained from the acoustic-wave-probe resin composition, the resin sheet having an acoustic impedance close to that of a living body, having a reduced acoustic wave attenuation even at high frequencies, and having a high tear strength.

SUMMARY OF THE INVENTION

The above-described composition in JP1987-89765A (JP-S62-89765A) can achieve, to a certain degree, a reduction in the amount of mineral filler added. However, since the composition still includes a small amount of mineral filler, the resultant sheet tends to scatter ultrasonic waves at high frequencies, which results in an increase in the acoustic wave attenuation. On the other hand, the above-described composition in WO2017/170215A improves the tear strength of the resin sheet. However, in consideration of the mechanical strength of acoustic wave probes recently in demand, the resin sheet needs further improvement in the tear strength.

Under such circumstances, an object of the present invention is to provide a resin material that provides a resin shaped article (such as a resin sheet) having an acoustic impedance close to that of a living body, a reduced acoustic wave attenuation even at high frequencies (such as 10 MHz), and high hardness and high tear strength, and that is suitable as a lens material for acoustic wave probes.

Another object of the present invention is to provide an acoustic lens, an acoustic wave probe, an acoustic wave determination device, an ultrasound diagnostic apparatus, a photo-acoustic wave determination device, and an ultrasonic endoscope that employ the above-described resin material as a constituent material. Another object of the present invention is to provide a method for producing the above-described acoustic lens.

The inventors of the present invention performed thorough studies and, as a result, have found that the above-described objects are achieved using a resin material containing a crosslinked form of a specific polymer having a moiety having a polysiloxane bond, and a moiety having at least one of an ester bond, an amide bond, a urethane bond, a urea bond, or an aromatic-ring-vinyl-derived structure. On the basis of this finding, the inventors have accomplished the present invention.

The above-described objects are achieved by the following means.

<1>

An acoustic-wave-probe resin material including a polymer that includes (a) a moiety having a polysiloxane bond, and (b) a moiety having at least one of an ester bond, an amide bond, a urethane bond, a urea bond, or an aromatic-ring-vinyl-derived structure, and that has a gel fraction of 60 mass % or more.

<2>

The acoustic-wave-probe resin material according to <1>, wherein the polymer has, in a side chain, any one of an ester bond, an amide bond, a urethane bond, a urea bond, and an aromatic ring.

<3>

The acoustic-wave-probe resin material according to <1> or <2>, wherein, in the polymer, at least a portion of the moiety (b) is (b1) an acryloyloxy structure unit, (b2) an acrylamide structure unit, or (b3) a styrene structure unit.

<4>

The acoustic-wave-probe resin material according to <3>, wherein the moiety (a) is represented by Formula (1) below, the acryloyloxy structure unit (b1) is represented by Formula (2) below, the acrylamide structure unit (b2) is represented by Formula (3) below, and the styrene structure unit (b3) is represented by Formula (4) below,

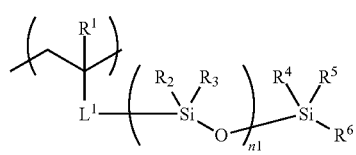

Formula (1)

where $R^1$ to $R^6$ each independently represent a hydrogen atom or a monovalent organic group, $L^1$ represents a divalent linking group, and n1 represents an integer of 3 to 10,000,

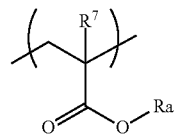

Formula (2)

where $R^7$ and Ra each independently represent a hydrogen atom or a monovalent organic group,

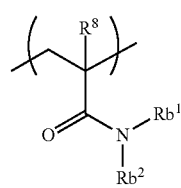

Formula (3)

where $R^8$, $Rb^1$, and $Rb^2$ each independently represent a hydrogen atom or a monovalent organic group, and

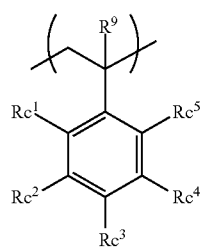

Formula (4)

where $R^9$ and $Rc^1$ to $Rc^5$ each independently represent a hydrogen atom, a halogen atom, or a monovalent organic group.

<5>

The acoustic-wave-probe resin material according to any one of <1> to <4>, wherein, in the polymer, at least a portion of the moiety (b) has at least one of an ester bond or an aromatic-ring-vinyl-derived structure.

<6>

The acoustic-wave-probe resin material according to any one of <1> to <5>, wherein the polymer contains a fluorine atom.

<7>

The acoustic-wave-probe resin material according to any one of <1> to <6>, wherein the moiety (b) has 5 or more fluorine atoms.

<8>

An acoustic lens including the acoustic-wave-probe resin material according to any one of <1> to <7>.

<9>

An acoustic wave probe including the acoustic lens according to <8>.

<10>

An acoustic wave determination device including the acoustic wave probe according to <9>.

<11>

An ultrasound diagnostic apparatus including the acoustic wave probe according to <9>.

<12>

A photo-acoustic wave determination device including the acoustic lens according to <8>.

<13>

An ultrasonic endoscope including the acoustic lens according to <8>.

<14>

A method for producing the acoustic lens according to <8>, the method including a step of, using heat or radiation, crosslinking a polymer including (a) a moiety having a polysiloxane bond, and (b) a moiety having at least one of an ester bond, an amide bond, a urethane bond, a urea bond, or an aromatic-ring-vinyl-derived structure.

In this Specification, unless otherwise specified, when a general formula representing a compound has a plurality of groups denoted by the same symbol, these may be the same or different, and, in the groups, specified groups (such as alkyl groups) may further have a substituent. "Si—H group" means a group having, on the silicon atom, three direct bonds in addition to —H; however, these direct bonds are abbreviated to simplify the description.

In this Specification, "acryl or acryloyl" broadly means a group of structures having an acryloyl group, and includes a structure having, at the a position, a substituent (such as an alkyl group).

In this Specification, the meaning of a value "to" a value is to include these values as the lower-limit value and the upper-limit value.

Incidentally, in this Specification, mass-average molecular weight is, unless otherwise specified, a value measured by gel permeation chromatography (Gel Permeation Chromatography: GPC) (polystyrene equivalent).

Specifically, mass-average molecular weight can be measured by preparing a GPC apparatus HLC-8220 (manufactured by Tosoh Corporation); using, as the eluant, tetrahydrofuran (manufactured by Wako Pure Chemical Industries, Ltd.); using, as the columns, TSKgel (registered trademark) G3000HXL+TSKgel (registered trademark) G2000HXL; and performing measurement using an R1 detector under conditions of a temperature of 23° C. and a flow rate of 1 mL/min.

An acoustic-wave-probe resin material according to the present invention can provide, when shaped, a resin shaped article in which an acoustic impedance close to that of a living body is achieved, a reduction in the acoustic wave attenuation even at high frequencies is achieved, and improved hardness and tear strength are achieved. This can provide an acoustic lens, an acoustic wave probe, an acoustic wave determination device, an ultrasound diagnostic apparatus, a photo-acoustic wave determination device, and an ultrasonic endoscope that have high acoustic-wave transmission and reception performance, and have good mechanical characteristics.

An acoustic lens, an acoustic wave probe, an acoustic wave determination device, an ultrasound diagnostic apparatus, a photo-acoustic wave determination device, and an ultrasonic endoscope according to the present invention have members formed from an acoustic-wave-probe resin material according to the present invention, so that the acoustic impedance is close to that of a living body, the acoustic wave attenuation can also be effectively suppressed, and the mechanical strength is also high.

A method for producing an acoustic lens according to the present invention can provide the above-described acoustic lens.

BRIEF DESCRIPTION OF THE DRAWING

The FIGURE is a perspective view of an example of a convex ultrasonic wave probe serving as an embodiment of the acoustic wave probe.

DESCRIPTION OF THE PREFERRED EMBODIMENTS

Acoustic-Wave-Probe Resin Material

An acoustic-wave-probe resin material according to the present invention (hereafter, also simply referred to as "resin material", or further abbreviated as "resin") contains a polymer (hereafter, also referred to as "polymer (A)") that includes (a) a moiety having a polysiloxane bond, and (b) a moiety having at least one of an ester bond, an amide bond, a urethane bond, a urea bond, or an aromatic-ring-vinyl-derived structure, and that has a gel fraction of 60 mass % or more (preferably 70 mass % or more, more preferably 80 mass % or more, still more preferably 85 mass % or more). The gel fraction may be 100 mass %.

The gel fraction is a value determined by a calculation method described in EXAMPLES. Incidentally, this gel fraction is calculated from the mass of the polymer or a crosslinked form of the polymer.

In the descriptions of the present invention, the aromatic-ring-vinyl-derived structure means a constituent component of the polymer formed by addition polymerization of a vinyl group of an aromatic-ring vinyl compound.

Hereafter, the moiety (a) having a polysiloxane bond is also simply referred to as "moiety (a)". The moiety (b) having at least one of an ester bond, an amide bond, a urethane bond, a urea bond, or an aromatic-ring-vinyl-derived structure is also simply referred to as "moiety (b)".

Incidentally, "an ester bond, an amide bond, a urethane bond, or a urea bond" may be included in a monovalent group.

The specific structure of the polymer (A) is not particularly limited, and may be, for example, a random, block, or graft polymer.

An acoustic-wave-probe resin material according to the present invention may have a form composed of the polymer (A), or may have a form formulated to include, in addition to the polymer (A), as long as advantages of the present invention are not hindered, as described later, commonly used additives or optional components exhibiting auxiliary effects, for example, organosiloxanes such as vinylsilicone and hydrosilicone, fillers, catalysts, solvents, dispersing agents, pigments, dyes, antistatic agents, flame retardants, and thermal conductivity improvers. When an acoustic-wave-probe resin material according to the present invention is constituted by two or more components, it preferably has the form of a composition in which the components are homogeneously mixed.

An acoustic-wave-probe resin material according to the present invention may be mixed with, for example, a solvent to have a form having fluidity, or may be shaped into a predetermined shape to have the form of pellets.

An acoustic-wave-probe resin material according to the present invention is shaped to thereby be suitably used as a constituent material for a member constituting an acoustic wave probe that has an acoustic impedance close to that of a living body, a reduction in the acoustic wave attenuation (in particular, acoustic wave attenuation at high frequencies), and good characteristics of hardness and tear strength.

In the case of using silicone resin alone, the acoustic wave attenuation is sufficiently reduced whereas the hardness and the tear strength are low. Such low hardness is inferentially resulted from the absence of a filler or a high-hardness structure in the resin. By contrast, in the polymer (A) used for the present invention, a hard segment is introduced into the polymer and, the polymer (A) is intramolecularly or intermolecularly crosslinked (to a gel fraction of 60 mass % or more), so that, without making the resin contain the filler or the like, the hardness and the tear strength of the resultant resin shaped article can be effectively improved. Thus, a reduced acoustic wave attenuation, and a high hardness and a high tear strength can be all achieved. In addition, in the polymer (A) used for the present invention, an element or structure having a high specific gravity can be introduced into the hard segment of the polymer. As a result, such an acoustic-wave-probe resin material according to the present invention can be processed into a resin shaped article that has an acoustic impedance close to that of a living body.

Thus, an acoustic-wave-probe resin material according to the present invention enables, even without containing mineral filler, production of a resin shaped article exhibiting the above-described good characteristics.

When the ester bond, the amide bond, the urethane bond, the urea bond, or the aromatic ring is located on a side chain of the polymer, compared with on the main chain of the polymer, the molecular mobility is lowered to achieve a reduction in the acoustic wave attenuation. For this reason, the polymer (A) preferably has, on a side chain, any one of the ester bond, the amide bond, the urethane bond, the urea bond, and the aromatic ring.

Incidentally, the polymer (A) has the polysiloxane bond on the main chain or on a side chain, preferably on a side chain.

The term "main chain" used herein means, among all the molecular chains in the polymer (A), a linear molecular chain in which all the molecular chains (long molecular chains and/or short molecular chains) except for the side chains can be regarded as pendants on the main chain. Typically, among the molecular chains constituting the polymer (A), the longest chain is the main chain. For example, in Polymerization reaction formula (1) described later, in Polymer 1 serving as the product, the repeating ethylene chains in parentheses constitute the main chain, and the other structures are side chains. In Polymerization reaction formula (2) described later, in Polymer 13 serving as the product, the ethylene chains in parentheses and "—[—X²—(—Si—O—)—X³]—" constitute the main chain and the other structures are side chains.

(a) Moiety Having Polysiloxane Bond

In the polymer (A) used for the present invention, the structure unit (a) is not particularly limited as long as it is a moiety having a polysiloxane bond. The moiety (a) is preferably a structure unit represented by Formula (1) below.

Incidentally, in the descriptions of the present invention, when the moiety having a polysiloxane bond has an ester bond, an amide bond, a urethane bond, a urea bond, or an aromatic-ring-vinyl-derived structure, it is classified as not the moiety (b), but as the moiety (a).

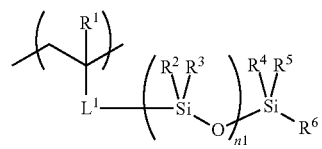

Formula (1)

In the formula, $R^1$ to $R^6$ each independently represent a hydrogen atom or a monovalent organic group, $L^1$ represents a divalent linking group, n1 preferably represents an integer of 3 to 10,000, more preferably an integer of 10 to 500, particularly preferably an integer of 50 to 300. This is because, when n1 satisfies such a range, the mobility in response to acoustic waves is low or the compatibility with the hard segments is high, to thereby suppress phase separation, so that a reduction in the acoustic wave attenuation is sufficiently achieved.

Examples of the monovalent organic group represented by $R^1$ to $R^6$ include an alkyl group, a cycloalkyl group, an alkenyl group, an aryl group, a heteroaryl group, an alkoxy group, an aryloxy group, a heteroaryloxy group, an alkylthio group, an arylthio group, a heteroarylthio group, an alkylamino group, an arylamino group, a heteroarylamino group, an alkyloxycarbonyl group, an aryloxycarbonyl group, a heteroaryloxycarbonyl group, an alkylaminocarbonyl group, an arylaminocarbonyl group, a heteroarylaminocarbonyl group, and a halogen group; preferred is any one of an alkyl group, a cycloalkyl group, an alkenyl group, and an aryl group. The following are detailed descriptions.

In the alkyl groups represented by $R^1$ to $R^5$, the number of carbon atoms is preferably 1 to 10, more preferably 1 to 4, still more preferably 1 or 2, particularly preferably 1. In the alkyl group represented by $R^6$, the number of carbon atoms is preferably 1 to 10, more preferably 1 to 8, particularly preferably 1 to 4. Examples of such alkyl groups include methyl, ethyl, n-propyl, isopropyl, n-butyl, isobutyl, n-hexyl, n-octyl, 2-ethylhexyl, and n-decyl.

In the cycloalkyl group, the number of carbon atoms is preferably 3 to 10, more preferably 5 to 10, still more preferably 5 or 6. The cycloalkyl group is preferably a three-membered ring, a five-membered ring, or a six-membered ring, more preferably a five-membered ring or a six-membered ring. Examples of the cycloalkyl group include cyclopropyl, cyclopentyl, and cyclohexyl.

In the alkenyl group, the number of carbon atoms is preferably 2 to 10, more preferably 2 to 4, still more preferably 2. Examples of the alkenyl group include vinyl, allyl, and butenyl.

In the aryl group, the number of carbon atoms is preferably 6 to 12, more preferably 6 to 10, still more preferably 6 to 8. Examples of the aryl group include phenyl, tolyl, and naphthyl.

Such an alkyl group, a cycloalkyl group, an alkenyl group, and an aryl group may have substituents. Examples of the substituents include halogen atoms (such as a fluorine atom, a chlorine atom, a bromine atom, and an iodine atom), alkyl groups, cycloalkyl groups, alkenyl groups, aryl groups, alkoxy groups, aryloxy groups, alkylthio groups, arylthio groups, a silyl group, and a cyano group.

Examples of such a group having a substituent include fluoroalkyl groups.

$R^1$ to $R^6$ are preferably alkyl groups, alkenyl groups, or aryl groups, more preferably alkyl groups having 1 to 4 carbon atoms. $R^1$ to $R^5$ are, from the viewpoint of a reduction in the acoustic wave attenuation, particularly preferably methyl groups; $R^6$ is preferably a butyl group.

In $L^1$, the divalent linking group is not particularly limited as long as advantages of the present invention are provided; examples include a single bond, an ester group (ester bond), alkylene groups (the number of carbon atoms is preferably 1 to 12, more preferably 1 to 8, still more preferably 1 to 6, particularly preferably 1 to 3; specific examples include methylene, ethylene, n-propylene, isopropylene, n-butylene, t-butylene, and n-octylene), arylene groups (the number of carbon atoms is preferably 6 to 18, more preferably 6 to 14, particularly preferably 6 to 12; specific examples include phenylene, tolylene, and naphthylene), oxyalkylene groups (the number of carbon atoms is preferably 1 to 12, more preferably 1 to 8, still more preferably 1 to 6, particularly preferably 1 to 3; specific examples include oxymethylene, oxyethylene, oxypropylene, and oxydimethylethylene), and oxyarylene groups (the number of carbon atoms is preferably 6 to 18, more preferably 6 to 14, particularly preferably 6 to 12; specific examples include oxyphenylene, oxytolylene (the tolylene is a divalent toluene), and oxynaphthylene), and combinations of the foregoing; preferred are an ester group, alkylene groups, oxyalkylene groups, and combinations of these. Specific examples of the combinations include a "-carbonyloxy-alkylene group-".

Each of such an oxyalkylene group and an oxyarylene group may bond to, on its one side or the other side, the adjacent Si; preferably, the alkylene group of the oxyalkylene group and the arylene group of the oxyarylene group bond to the adjacent Si, and are more preferably an ethylene group, a propylene group, and a phenylene group. In the above-described "-carbonyloxy-alkylene group-", the alkylene group preferably bonds to the adjacent Si.

(b) Moiety Having at Least One of Ester Bond, Amide Bond, Urethane Bond, Urea Bond, or Aromatic-Ring-Vinyl-Derived Structure The polymer (A) has, in addition to the moiety (a), the moiety (b) having at least one of an ester bond, an amide bond, a urethane bond, a urea bond, or an aromatic-ring-vinyl-derived structure. The moiety (b) is preferably (b1) an acryloyloxy structure unit, (b2) an acrylamide structure unit, or (b3) a styrene structure unit. Specifically, the polymer (A) ordinarily has, in its structure, a plurality of moieties (b), and, preferably, the moieties (b) present in the polymer (A) are at least partially the acryloyloxy structure unit (b1), the acrylamide structure unit (b2), or the styrene structure unit (b3). Preferably, the moieties (b) present in the polymer (A) are at least partially at least one of the acryloyloxy structure unit (b1) or the styrene structure unit (b3).

In order to further improve at least acoustic characteristics and/or mechanical strength, the moiety (b) is preferably the styrene structure unit (b3) or a combination of the acryloyloxy structure unit (b1) and the styrene structure unit (b3).

In the polymer (A), in order to improve the hardness and the tear strength of the moiety (b), the moiety (b) preferably has at least one of an ester bond or an aromatic-ring-vinyl-derived structure.

Hereafter, the acryloyloxy structure unit (b1) is also simply referred to as "structure unit (b1)". The acrylamide structure unit (b2) is also simply referred to as "structure unit (b2)". The styrene structure unit (b3) is also simply referred to as "structure unit (b3)".

(b1) Acryloyloxy Structure Unit

In the polymer (A) used in the present invention, the structure unit (b1) is preferably a structure unit represented by the following Formula (2).

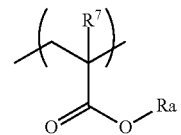

Formula (2)

In the formula, $R^7$ and Ra each independently represent a hydrogen atom or a monovalent organic group.

The monovalent organic group represented by $R^7$ may be the monovalent organic group represented by $R^1$ in Formula (1) above.

$R^7$ is preferably a hydrogen atom or an alkyl group. The number of carbon atoms of the alkyl group is preferably 1 to 10, more preferably 1 to 4, still more preferably 1 or 2, particularly preferably 1. Examples of the alkyl group include methyl, ethyl, n-propyl, isopropyl, n-butyl, isobutyl, n-hexyl, n-octyl, 2-ethylhexyl, and n-decyl.

Specific examples of the monovalent organic group represented by Ra include the monovalent organic group represented by $R^1$ in Formula (1) above.

Ra is preferably a hydrogen atom, an alkyl group, or an aryl group.

The number of carbon atoms of the alkyl group is preferably 1 to 10, more preferably 1 to 6. Examples of the alkyl group include methyl, ethyl, n-propyl, isopropyl, n-butyl, isobutyl, n-hexyl, n-octyl, 2-ethylhexyl, and n-decyl.

The number of carbon atoms of the aryl group is preferably 6 to 12, more preferably 6 to 10, still more preferably 6 to 8, particularly preferably 6. Examples of the aryl group include phenyl, tolyl, and naphthyl.

The monovalent organic groups represented by $R^7$ and Ra may have substituents. Examples of the substituents include halogen atoms (such as a fluorine atom, a chlorine atom, a bromine atom, and an iodine atom), alkyl groups, cycloalkyl groups, alkenyl groups (preferably a vinyl group), aryl groups, alkoxy groups, aryloxy groups, alkylthio groups, arylthio groups, a silyl group, a cyano group, an epoxy group, and a ureido group, and combinations of the foregoing.

From the viewpoint of reducing the acoustic wave attenuation and achieving the acoustic impedance closer to that of a living body, preferred are halogen atoms, in particular, more preferred is a fluorine atom.

Examples of the groups having substituents include alkylureidoalkyl groups, alkyl groups having fluorine atoms, and aryl groups having fluorine atoms.

(b2) Acrylamide Structure Unit

In the polymer (A) used for the present invention, the structure unit (b2) is preferably a structure unit represented by the following Formula (3).

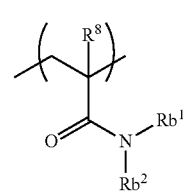

Formula (3)

In the formula, $R^8$, $Rb^1$, and $Rb^2$ each independently represent a hydrogen atom or a monovalent organic group.

Specific examples of the monovalent organic group represented by $R^8$ include the monovalent organic group represented by IV in Formula (I) above.

$R^8$ is preferably a hydrogen atom or an alkyl group, more preferably an alkyl group. The number of carbon atoms of the alkyl group is preferably 1 to 10, more preferably 1 to 4, still more preferably 1 or 2, particularly preferably 1. Examples of the alkyl group include methyl, ethyl, n-propyl, isopropyl, n-butyl, isobutyl, n-hexyl, n-octyl, 2-ethylhexyl, and n-decyl.

The monovalent organic groups represented by $R^5$, $Rb^1$, and $Rb^2$ may have substituents. Examples of the substituents include halogen atoms, alkyl groups, cycloalkyl groups, alkenyl groups, aryl groups, alkoxy groups, aryloxy groups, alkylthio groups, arylthio groups, a silyl group, and a cyano group.

Examples of the groups having substituents include alkyl groups having fluorine atoms and perfluoroaryl groups.

(b3) Styrene Structure Unit

In the polymer (A) used for the present invention, the structure unit (b3) is preferably a structure unit represented by the following Formula (4).

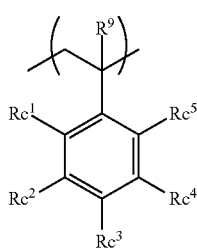

Formula (4)

In the formula, $R^9$ and $Rc^1$ to $Rc^5$ each independently represent a hydrogen atom, a halogen atom, or a monovalent organic group.

Specific examples of the monovalent organic group represented by $R^9$ include the monovalent organic group represented by $R^1$ in Formula (I) above. $R^9$ is preferably a hydrogen atom.

Specific examples of the monovalent organic groups represented by $Rc^1$ to $Rc^5$ include the monovalent organic group represented by $R^1$ in Formula (1) above.

$Rc^1$ to $Rc^5$ are preferably hydrogen atoms or halogen atoms.

The number of carbon atoms of such an alkyl group is preferably 1 to 10, more preferably 1 to 4, still more preferably 1 or 2, particularly preferably 1. Examples of the alkyl group include methyl, ethyl, n-propyl, isopropyl, n-butyl, isobutyl, n-hexyl, n-octyl, 2-ethylhexyl, and n-decyl.

Such a halogen atom is preferably a fluorine atom or a bromine atom, more preferably a fluorine atom.

The monovalent organic groups represented by $R^9$ and $Rc^1$ to $Rc^5$ may have substituents. Examples of the substituents include halogen atoms, alkyl groups, cycloalkyl groups, alkenyl groups, aryl groups, alkoxy groups, aryloxy groups, alkylthio groups, arylthio groups, a silyl group, and a cyano group.

Examples of the groups having substituents include alkyl groups having fluorine atoms and aryl groups having fluorine atoms.

In the polymer (A) used for the present invention, preferably, the moiety (a) is represented by Formula (1) above, the structure unit (hi) is represented by Formula (2) above, the structure unit (b2) is represented by Formula (3) above, and the structure unit (b3) is represented by Formula (4) above. This is because the polymer (A) has a structure that is less likely to respond to acoustic waves to sufficiently achieve a reduction in the acoustic wave attenuation; in addition, the polymer (A) has a rigid structure, to thereby achieve improved mechanical strength (hardness).

The polymer (A) used for the present invention is also preferably a block polymer constituted by a block of the moiety (a) and at least one block of the moiety (b) because the polymer has, as a whole, lowered mobility, and has high mechanical strength (hardness).

In the block polymer, preferably, the moiety (a) is represented by the following Formula (5), and the moiety (b) is represented by Formula (4) above because the hardness is high. Another reason is that the structure unit represented by Formula (5) and the structure unit represented by Formula (4) have high compatibility with each other to suppress phase separation, to sufficiently achieve a reduction in the acoustic wave attenuation.

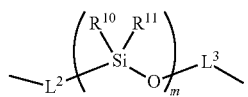

Formula (5)

In the formula, $R^{10}$ and $R^{11}$ each independently represent a hydrogen atom or a monovalent organic group; $L^2$ and $L^3$ each independently represent a divalent linking group; and m represents an integer of 3 to 10,000.

The organic groups represented by $R^{10}$ and $R^{11}$ have the same definitions and preferred ranges as in the monovalent organic group represented by $R^1$ in Formula (1) above.

The linking groups represented by $L^2$ and $L^3$ have the same definitions and preferred ranges as in the linking group represented by $L^1$ in Formula (1) above. However, the structure unit represented by Formula (5) does not include "—O—O—".

m is preferably an integer of 10 to 1000, more preferably an integer of 50 to 300.

The polymer (A) used for the present invention, from the viewpoint of reducing the acoustic wave attenuation and increasing the acoustic wave impedance, preferably has a fluorine atom; in particular, preferably, the moiety (b) has a fluorine atom. In addition, in order to further increase the density, the moiety (b) preferably has 5 or more fluorine atoms; preferably, the acryloyloxy structure unit (b1), the acrylamide structure unit (b2), and the styrene structure unit (b3) each have 5 or more fluorine atoms.

The polymer (A) preferably has a fluorine atom content of 1 to 100 mmol/g, more preferably 2 to 50 mmol/g, still more preferably 3 to 20 mmol/g.

The fluorine atom content in the polymer (A) can be calculated by analyzing the compositional ratio of the polymer by NMR.

Incidentally, the fluorine atom content of the polymer (A) present in, for example, an acoustic lens can also be measured by an analysis method such as NMR or elemental analysis.

Specific examples of the structure unit having a fluorine atom that may be employed as the moiety (b) include the following compounds.

Examples of the acryloyloxy structure unit (b1) include structure units derived from pentafluorophenyl methacrylate, 2,2,2-trifluoroethyl methacrylate, 2,2,2-trifluoropropyl methacrylate, 2,2,3,3,3-pentafluoropropyl methacrylate, 1H,1H,2H,2H-nonafluorohexyl methacrylate, 2-(perfluorobutyl)ethyl methacrylate, 3-(perfluorobutyl)-2-hydroxypropyl methacrylate, 2-(perfluorooctyl)ethyl methacrylate, 3-(perfluorooctyl)-2-hydroxypropyl methacrylate, 2-(perfluorodecyl)ethyl methacrylate, 2-(perfluoro-3-methylbutyl) ethyl methacrylate, 3-(perfluoro-3-methylbutyl)-2-hydroxypropyl methacrylate, 2-(perfluoro-5-methylhexyl)ethyl methacrylate, 3-(perfluoro-5-methylhexyl)-2-hydroxypropyl methacrylate, 2-(perfluoro-7-methyl octyl)ethyl methacrylate, 3-(perfluoro-7-methyloctyl)ethyl methacrylate, tetrafluoropropyl methacrylate, octafluoropentyl methacrylate, dodecafluoroheptyl methacrylate, hexadecafluorononyl methacrylate, 1-(trifluoromethyl)trifluoroethyl methacrylate, hexafluorobutyl methacrylate, pentafluorophenoxy methacrylate, 1,1,1,3,3,3-hexafluoroisopropyl methacrylate, pentafluorobenzyl methacrylate, methyl α-trifluoromethylmethacrylate, 2,2,2-trifluoroethyl acrylate, 2,2,3,3,3-pentafluoropropyl acrylate, 2-(perfluorobutyl)ethyl acrylate, 3-(perfluorobutyl)-2-hydroxypropyl acrylate, 2-(perfluorohexyl)ethyl acrylate, 3-(perfluorohexyl)-2-hydroxypropyl acrylate, 2-(perfluorooctyl)ethyl acrylate, 3-(perfluorooctyl)-2-hydroxypropyl acrylate, 2-(perfluorodecyl)ethyl acrylate, 2-(perfluoro-3-methylbutyl)ethyl acrylate, 3-(perfluoro-3-methoxybutyl)-2-hydroxypropyl acrylate, 2-(perfluoro-5-methylhexyl)ethyl acrylate, 3-(perfluoro-5-methylhexyl)-2-hydroxypropyl acrylate, 2-(perfluoro-7-methyloctyl)-2-hydroxypropyl acrylate, tetrafluoropropyl acrylate, octafluoropentyl acrylate, or dodecafluoroheptyl acrylate.

Examples of the acrylamide structure unit (b2) include structure units derived from N,N-bis(perfluoromethyl)acrylamide, N-(perfluoroisopropyl)acrylamide, or N-(perfluoro t-butyl)acrylamide.

Examples of the styrene structure unit (b3) include structure units derived from p-fluorostyrene, pentafluorostyrene, or 3,5-bis(trifluoromethyl)styrene.

In the polymer (A) used for the present invention, when the moiety (b) is an acryloyloxy structure unit, a dipole-dipole interaction between esters of the acryloyloxy structures increases the intermolecular interaction of the polymer to achieve higher hardness. In addition, the copolymerizability with the moiety (a) is improved, to thereby improve the compatibility between the moiety (a) and the acryloyloxy structure unit, to achieve further improvement in the acoustic wave attenuation.

In the polymer (A) used for the present invention, when the moiety (b) is a styrene structure unit, a nonpolar structure is provided. Thus, the compatibility with the moiety (a) is improved, so that a reduction in the acoustic wave attenuation is sufficiently achieved. From this viewpoint, the moiety (b) preferably includes the styrene structure unit (b3).

The moiety (b) present in the polymer (A) may be one species or two or more species. The polymer (A) may have, among the structure units (b1) to (b3), one species or two or more species in combination.

The polymer (A) used for the present invention, in order to increase the mechanical strength, preferably contains a high-Tg structure (structure having a high glass transition temperature (Tg)). Use of a combination of a fluorine-containing structure unit and the high-Tg structure provides effective improvements in acoustic characteristics and mechanical strength. The high-Tg structure is a polymer structure. The constitutional unit of the polymer structure that is a high-Tg structure is preferably selected such that, in the case of employing a homopolymer constituted by this constitutional unit alone, this homopolymer has a Tg of 60° C. or more, more preferably 80° C. or more. The upper limit of the Tg of this homopolymer is practically 200° C. or less. In the calculation of Tg, the homopolymer employed above is estimated to have a degree of polymerization of 300. Examples of the constitutional unit having a high-Tg structure include a methacrylate structure unit, a styrene structure unit, a methacrylamide structure unit, a structure unit having an alicyclic structure, and a structure unit having an aromatic ring.

In the polymer (A), the percentage of the moiety (a) having a polysiloxane bond is, from the viewpoint of making the acoustic impedance be close to that of a living body, and reducing the acoustic wave attenuation, preferably 20 mass % or more, more preferably 20 to 90 mass %, more preferably 30 to 80 mass %, still more preferably 40 to 60 mass %. Alternatively, the percentage is also preferably 40 to 90 mass %.

In the polymer (A), the percentage of the moiety (b) is, from the viewpoint of imparting high hardness and from the viewpoint of making the acoustic impedance be close to that of a living body, preferably 10 to 80 mass %, more preferably 20 to 80 mass %, preferably 20 to 70 mass %, still more preferably 30 to 60 mass %. Alternatively, the percentage is also preferably 10 to 60 mass %.

In the polymer (A), the contents of the moiety (a) and the moiety (b) can be calculated on the basis of, for example, the amounts of the monomers charged during synthesis (mass ratio).

In the polymer (A), the moiety (a) preferably has a mass-average molecular weight of 4,000 or more, more preferably 8,000 or more. The upper limit is not particularly limited, but is preferably 50,000 or less, more preferably 30,000 or less.

This is because, when the mass-average molecular weight of the moiety (a) satisfies such a range, the acoustic wave attenuation can be more effectively reduced.

The mass-average molecular weight of the polymer (A) can be measured by, for example, performing NMR analysis of the polymer (A), or subjecting the polymer (A) to hydrolysis treatment and GPC measurement.

An acoustic-wave-probe resin material according to the present invention preferably has an acoustic impedance close to that of a living body, more preferably 1.3 Mrayls or more, that is, $1.30 \times 10^6$ kg/m$^2$/s or more. Thus, the polymer (A) preferably has a density of 1.05 g/cm$^3$ or more, more preferably 1.10 g/cm$^3$ or more. The upper limit of the density is not particularly limited, but is preferably 1.90 g/cm$^3$ or less, more preferably 1.60 g/cm$^3$ or less.

These density values are each determined by rounding off the third decimal place. The density of the polymer (A) can be determined by, for example, measurement according to a method described in EXAMPLES described later, or by calculation from the densities of the monomers.

The acoustic-wave-probe resin material preferably has a polymer (A) content of 50 to 100 mass %, more preferably 80 to 100 mass %, still more preferably 90 to 100 mass %.

The polymer (A) used for the present invention also preferably has a moiety other than the moiety (a) and other than the moiety (b) (hereafter, referred to as "other moiety").

The other moiety can be introduced without particular limitations as long as advantages of the present invention are provided, and may be, for example, a moiety having at least one of an imide bond or an ether bond.

In the polymer (A), the percentage of the other moiety is, from the viewpoint of reducing the acoustic wave attenuation, preferably 0 to 30 mass %, more preferably 0 to 20 mass %.

The polymer (A) used for the present invention can be synthesized in a standard manner; for example, it can be obtained by causing, in a standard manner, a reaction between a monomer that can constitute or form the moiety (a), and a monomer that can constitute or form the moiety (b), and crosslinking the resultant polymer (A)-forming polymer in a standard manner. The polymerization reaction may be performed by, for example, anionic polymerization, cationic polymerization, radical polymerization, polyaddition, or polycondensation.

The moiety having a urethane bond can be obtained by, for example, a polyaddition reaction between a diisocyanate compound and a diol compound. The moiety having a urea bond can be obtained by a polyaddition reaction between a diisocyanate compound and a diamine compound. Alternatively, for example, a reaction is caused between an isocyanato group of an acrylic compound having the isocyanato group in the side chain and a hydroxy group of an alcohol compound or an amino group of an amine compound, and the resultant acrylic compound having, in the side chain, a urethane bond or a urea bond is subjected to chain polymerization, to thereby obtain a moiety having, in the side chain, a urethane bond or a urea bond.

The moiety having an ester bond can be obtained by, for example, a polycondensation reaction between a dicarboxylic acid compound and a diol compound. Alternatively, for example, a reaction is caused between a carboxy group of an acrylic compound having the carboxy group in the side chain and a hydroxy group of an alcohol compound, and the acrylic compound having an ester bond in the side chain is subjected to chain polymerization, to thereby obtain a moiety having an ester bond in the side chain.

Alternatively, a monomer that has a function of a polymerization initiator and that can constitute the structure unit (a) or can constitute the structure unit (b) may be used to synthesize the polymer (A)-forming polymer. An example is a polydimethylsiloxane unit-containing polymeric azo polymerization initiator VPS-1001 (trade name, manufactured by Wako Pure Chemical Industries, Ltd.).

The polymer (A) used for the present invention may be one species alone, or two or more species in combination.

An acoustic-wave-probe resin material according to the present invention may appropriately include, in addition to the polymer (A), for example, organosiloxanes such as vinylsilicone and hydrosilicone, fillers, catalysts, solvents, dispersing agents, pigments, dyes, antistatic agents, flame retardants, and thermal conductivity improvers.

Method for Producing Acoustic-Wave-Probe Resin Material

An acoustic-wave-probe resin material according to the present invention may be the polymer (A) itself. Alternatively, in the case of containing, in addition to the polymer (A), the above-described components, the resin material can be prepared in a standard manner.

For example, it can be obtained by kneading the polymer (A) to be crosslinked and the above-described other optional components with a kneader, a press kneader, a Banbury mixer (continuous kneader), or a twin-roll kneader, subsequently performing shaping, and introducing a crosslinked structure. The order of mixing the components is not particularly limited.

Regarding an acoustic-wave-probe resin material according to the present invention, for example, at least the polymer (A)-forming polymer to be crosslinked and organic peroxide are added and mixed together; a shaping process such as heat-pressing is performed to shape the resin material into a desired shape and to cause crosslinking within the polymer (A)-forming polymer, to obtain an acoustic-wave-probe resin material (shaped article). The method of performing heat-pressing is not particularly limited, and can be performed in a standard manner. For example, an apparatus such as MINI TEST PRESS-10 (manufactured by Toyo Seiki Seisaku-sho, Ltd., trade name) may be used to perform heat-pressing at 50 to 200° C. for 1 to 10 minutes at a pressure of 5 to 30 MPa.

Alternatively, for example, at least the polymer (A)-forming polymer is heat-pressed into a desired shape, and subsequently irradiated with radiation to cause crosslinking within the polymer (A)-forming polymer, to obtain a resin material (shaped article) according to the present invention. Examples of the radiation include electron beams and γ-rays.

Alternatively, for example, when the moiety (b) has a crosslinking reaction group (such as an epoxy group or a vinyl group), to the resin material, a polymerization initiator (such as a cationic polymerization initiator) is added and mixed, and the resin material is subsequently heat-pressed to be shaped into a desired shape and to cause crosslinking within the polymer (A), to thereby obtain an acoustic-wave-probe resin shaped article.

The gel fraction of an acoustic-wave-probe resin material according to the present invention can be adjusted by changing, for example, the organic peroxide content, the heating temperature, the radiation dose, or the crosslinking reaction group content of the structure unit (b).

An acoustic-wave-probe resin material according to the present invention is useful for medical parts, and can be preferably used for, for example, acoustic wave probes and acoustic wave determination devices. Incidentally, an acoustic wave determination device according to the present invention is not limited to ultrasound diagnostic devices or photo-acoustic wave determination devices, and refers to devices that receive acoustic waves reflected by or generated in the target, and display the acoustic waves as images or signal intensities.

In particular, an acoustic-wave-probe resin material according to the present invention can be suitably used as, for example, in an ultrasound diagnostic apparatus, a material for an acoustic lens, or a material for an acoustic matching layer disposed between a piezoelectric element and an acoustic lens and having a function of achieving matching of acoustic impedance between the piezoelectric element and the acoustic lens; in a photo-acoustic wave determination device or an ultrasonic endoscope, a material for an acoustic lens; and, in an ultrasonic wave probe including, as an ultrasonic transducer array, capacitive micromachined ultrasonic transducers (cMUT: Capacitive Micromachined Ultrasonic Transducers), a material for an acoustic lens.

Specifically, an acoustic-wave-probe resin material according to the present invention is suitably applied to, for example, ultrasound diagnostic apparatuses described in, for example, JP2005-253751A and JP2003-169802A, and acoustic wave determination devices such as photo-acoustic wave determination devices described in, for example, JP2013-202050A, JP2013-188465A, JP2013-180330A, 0.11'2013-158435A, and JP2013-154139A.

Acoustic Wave Probe (Probe)

The configuration of an acoustic wave probe according to the present invention will be described further in detail below on the basis of the configuration of an ultrasonic wave probe of an ultrasound diagnostic apparatus in the FIGURE.

Incidentally, the ultrasonic wave probe is a probe that particularly uses, as the acoustic waves in an acoustic wave probe, ultrasonic waves. Thus, the basic structure of the ultrasonic wave probe can be directly applied to acoustic wave probes.

Ultrasonic Wave Probe

An ultrasonic wave probe 10 is a main constituent part of an ultrasound diagnostic apparatus, and has functions of generating ultrasonic waves and transmitting and receiving ultrasonic wave beams. As illustrated in the FIGURE, the ultrasonic wave probe 10 has a configuration including, in sequence from the distal end (surface brought into contact with a living body serving as the determination target) portion, an acoustic lens 1, an acoustic matching layer 2, a piezoelectric element layer 3, and a backing member 4. Incidentally, in recent years, for the purpose of receiving higher-order harmonics, a laminate structure has been proposed in which a transmission ultrasonic transducer (piezoelectric element) and a reception ultrasonic transducer (piezoelectric element) are different from each other in constituent materials.

Piezoelectric Element Layer

The piezoelectric element layer 3 is a part that generates ultrasonic waves. Electrodes are bonded to both sides of a piezoelectric element. Upon application of a voltage, the piezoelectric element repeatedly lengthens, shortens, and expands to cause vibrations, to thereby generate ultrasonic waves.

As materials constituting such piezoelectric elements, single crystals of, for example, rock crystals, $LiNbO_3$, $LiTaO_3$, or $KNbO_3$, thin films of, for example, ZnO or AlN, and, what are called, ceramic inorganic piezoelectric bodies provided by subjecting sintered bodies such as $Pb(Zr,Ti)O_3$-based sintered bodies to polarization treatment are widely used. In general, piezoelectric ceramics such as PZT: lead titanate zirconate, which has high transduction efficiency, are used.

Piezoelectric elements for detecting reception waves at higher frequencies are required to have sensitivity for a broader band. Thus, as piezoelectric elements suitable for high frequencies and broad bands, organic piezoelectric bodies using organic polymeric substances such as polyvinylidene fluoride (PVDF) are used.

Furthermore, for example, JP2011-071842A describes a cMUT provided by the MEMS (Micro Electro Mechanical Systems) technology to have an array structure that exhibits good short-pulse characteristics and broad-band characteristics, is easily mass-produced, and has less variations in characteristics.

In the present invention, any of such piezoelectric element materials can be suitably used.

Backing Member

The backing member 4 is disposed on the back surface of the piezoelectric element layer 3, and suppresses an excess of vibrations to thereby achieve a decrease in the pulse width of ultrasonic waves, which contributes to an increase in the axial resolution for ultrasonographic images.

Acoustic Matching Layer

The acoustic matching layer 2 is disposed in order to reduce the difference in acoustic impedance between the piezoelectric element layer 3 and the determination target, to achieve efficient transmission and reception of ultrasonic waves.

An acoustic-wave-probe resin material according to the present invention has a small difference from the acoustic impedance (1.40 to $1.70 \times 10^6$ kg/m$^2$/sec) of a living body, and hence can be suitably used as a material for the acoustic matching layer. The acoustic matching layer preferably includes 10 mass % or more of an acoustic-wave-probe resin material according to the present invention.

The acoustic lens 1 is disposed in order to use refraction to focus ultrasonic waves in the slice direction to thereby improve resolution. The acoustic lens 1 is, during in contact with a living body serving as the determination target, required to make the ultrasonic waves match the acoustic impedance of the living body (in the case of the human body, 1.40 to $1.70 \times 10^6$ kg/m$^2$/sec); and the acoustic lens 1 itself is required to have a low ultrasonic wave attenuation.

Specifically, as a material for the acoustic lens 1, a material is used that provides an acoustic velocity sufficiently lower than the acoustic velocity in the human body, that causes less attenuation of ultrasonic waves, and that has an acoustic impedance close to that of the human skin. This results in an increase in the transmission and reception sensitivity for ultrasonic waves.

An acoustic-wave-probe resin material according to the present invention can also be suitably used as a material for such an acoustic lens.

Operations of the ultrasonic wave probe 10 having such a configuration will be described. A voltage is applied to electrodes disposed on both sides of the piezoelectric element to resonate the piezoelectric element layer 3, to transmit ultrasonic signals from the acoustic lens to the determination target. Upon reception, reflected signals (echo signals) from the determination target vibrate the piezoelectric element layer 3, and these vibrations are electrically transduced into signals to obtain images.

In particular, an acoustic lens formed from an acoustic-wave-probe resin material according to the present invention provides, in the case of being used as a general medical ultrasonic transducer, a marked effect of improving the sensitivity for ultrasonic transmission frequencies of about 5 MHz or more. In particular, for ultrasonic transmission frequencies of 10 MHz or more, an especially marked effect of improving the sensitivity is expected.

Hereinafter, apparatuses in which acoustic lenses obtained from an acoustic-wave-probe resin material according to the present invention particularly function to address the existing problems will be described in detail.

Incidentally, an acoustic-wave-probe resin material according to the present invention also exhibits marked advantages in apparatuses other than those described below.

Ultrasonic Wave Probe Including cMUT (Capacitive Micromachined Ultrasonic Transducers)

When the cMUT devices described in, for example, JP2006-157320A and JP2011-71842A are used for ultrasonic transducer arrays, the resultant sensitivity is generally lower than in transducers using a general piezoelectric ceramic (PZT).

However, by using an acoustic lens formed from an acoustic-wave-probe resin material according to the present invention, the sensitivity shortage of the cMUT can be compensated. As a result, the sensitivity of the cMUT can be made close to the performance of the existing transducers.

Incidentally, cMUT devices are produced by the MEMS technology, and hence are more easily mass-produced than piezoelectric ceramic probes. Thus, ultrasonic wave probes at low costs can be supplied to the market.

Photo-Acoustic Wave Determination Device Using Photo Acoustic Imaging

In the photo acoustic imaging (PAI: Photo Acoustic Imaging) described in, for example, JP2013-158435A, light (electromagnetic waves) is applied to the inside of the human body, the applied light causes adiabatic expansion of the human tissue, and the resultant ultrasonic waves are displayed as images or the signal intensities of the resultant ultrasonic waves are displayed.

In this case, the acoustic pressure of ultrasonic waves generated by applied light is very low, and hence it is difficult to observe deep portions of the human body, which has been a problem.

However, by using an acoustic lens formed from an acoustic-wave-probe resin material according to the present invention, this problem can be effectively addressed.

Ultrasonic Endoscope

Regarding ultrasonic transducers in ultrasonic endoscopes described in, for example, JP2008-311700A, since the structures inherently have longer signal cables than body-surface transducers, cable loss occurs and hence the sensitivity of the transducers needs to be improved, which has been a problem. Regarding this problem, it is said that there are no ways to effectively improve the sensitivity for the following reasons.

First, in the cases of body-surface ultrasound diagnostic apparatuses, for example, amplification circuits and AD converter ICs can be disposed at the tips of the transducers. By contrast, since ultrasonic endoscopes are used by being inserted into the body, the transducers have insufficient spaces for such disposition, so that it is difficult to dispose, for example, amplification circuits and AD converter ICs at the tips of the transducers.

Second, piezoelectric single-crystals employed for transducers for body-surface ultrasound diagnostic apparatuses are, because of their physical characteristics and process suitability, difficult to apply to transducers that transmit ultrasonic waves at frequencies of 7 to 8 MHz or more. However, regarding ultrasonic waves for endoscopes, since probes generally transmit ultrasonic waves at frequencies of 7 to 8 MHz or more, it is difficult to use piezoelectric single-crystal materials for improving the sensitivity.

However, by using an acoustic lens formed from an acoustic-wave-probe resin material according to the present invention, the sensitivity of endoscope ultrasonic transducers can be improved.

Alternatively, even in the case of using the same ultrasonic transmission frequency (for example, 10 MHz), when, in endoscope ultrasonic transducers, acoustic lenses formed from an acoustic-wave-probe resin material according to the present invention are used, effectiveness is particularly exerted.

Examples

Hereinafter, the present invention will be described further in detail on the basis of Examples using, as acoustic waves, ultrasonic waves. Incidentally, the present invention is not limited to ultrasonic waves, and may employ acoustic waves at audio frequencies as long as appropriate frequencies are selected in accordance with, for example, the determination target and determination conditions.

Examples

Synthesis of Polymers 1 to 4, c1, and c2 Used for Producing Resin Sheets 1 to 4, c1, and c2

To 50 parts by mass of single-end methacryl-modified silicone (trade name: KF-2012, manufactured by Shin-Etsu Silicone), 50 parts by mass of styrene, and 100 parts by mass of propylene glycol-1-monomethyl ether-2-acetate, at 80° C. under a nitrogen atmosphere, 0.1 parts by mass of dimethyl 1,1'-azobis(1-cyclohexanecarboxylate) (manufactured by Wako Pure Chemical Industries, Ltd.) was added, and a reaction was caused at 80° C. for 2 hours. Subsequently, 0.1 parts by mass of dimethyl 1,1'-azobis(1-cyclohexanecarboxylate) (manufactured by Wako Pure Chemical Industries, Ltd.) was added, and a reaction was caused at 80° C. for 2 hours. Furthermore, 0.1 parts by mass of dimethyl 1,1'-azobis(1-cyclohexanecarboxylate) (manufactured by Wako Pure Chemical Industries, Ltd.) was added, and a reaction was caused at 80° C. for 2 hours. The reaction solution was added to 1000 mL of isopropyl alcohol and 200 mL of methanol, to generate a white solid. The generated white solid was washed with methanol, and dried to obtain Polymers 1 to 4, c1, and c2. The polymerization reaction formula is described below.

In the following Polymerization reaction formula (1), the structures in the parentheses are repeating structures.

Polymerization reaction formula (1)

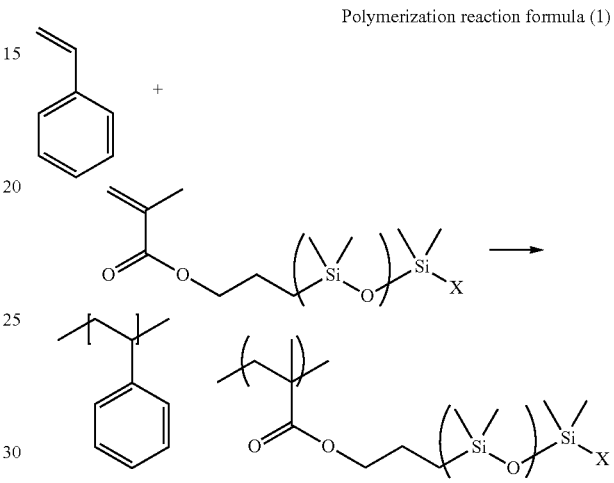

In the formula, X represents a monovalent organic group.

Synthesis of Polymers 5 to 12, 14, 15, 20 to 24, and c3 Used for Producing Resin Sheets 5 to 12, 14, 15, 20 to 24, and c3

The same procedures as in the synthesis of Polymer 1 were performed except for changes to the compositions of the moiety (a)-forming monomer and the moiety (b)-forming monomer in Table 1 described later, to synthesize Polymers 5 to 12, 14, 15, 20 to 24, and c3. As described later in Table 1, two or more moiety (b)-forming monomers were used for some of the polymers.

Synthesis of Polymer 13 Used for Producing Resin Sheet 13

A polydimethylsiloxane unit-containing polymeric azo polymerization initiator (50 parts by mass, trade name: VPS-1001, manufactured by Shin-Etsu Silicone), 20 parts by mass of styrene, 30 parts by mass of pentafluorostyrene, and 100 parts by mass of propylene glycol-1-monomethyl ether-2-acetate were mixed together, and caused to react at 75° C. under a nitrogen atmosphere for 4 hours. The reaction solution was added to 1000 mL of methanol, to generate a white solid. The generated white solid was washed with methanol, and dried to obtain Polymer 13. The polymerization reaction formula is described below.

In the following Polymerization reaction formula (2), the structures in parentheses are repeating structures.

Polymerization reaction formula (2)

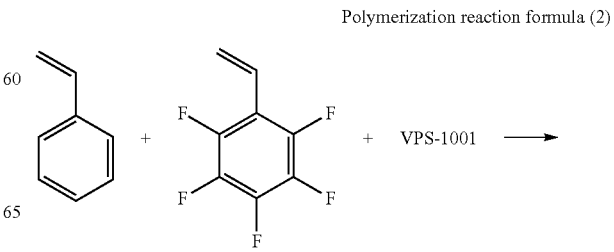

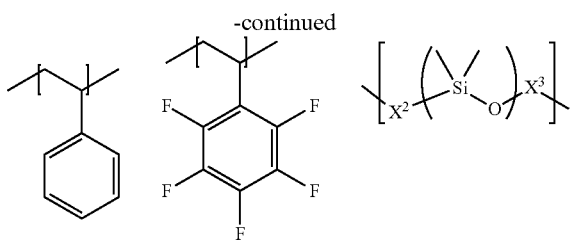

In the formula, $X^2$ and $X^3$ represent divalent organic groups.

Synthesis of Polymer 16 Used for Producing Resin Sheet 16

To 79 parts by mass of dual-end hydroxy-modified silicone (trade name: KF-6000, manufactured by Shin-Etsu Silicone), 50 parts by mass of tetrahydrofuran, and 50 parts by mass of N-methylpyrrolidone, 21 parts by mass of 4,4'-diphenylmethane diisocyanate and 0.1 parts by mass of K-KAT348 (trade name, manufactured by Kusumoto Chemicals, Ltd.) were added, and a reaction was caused at 70° C. for 1 hour. Subsequently, the reaction solution was added to 500 mL of methanol, to generate a white solid. The generated white solid was washed with water, washed with methanol, and dried to obtain Polymer 16.

Synthesis of Polymer 17 Used for Producing Resin Sheet 17

To 77 parts by mass of dual-end amino-modified silicone KF-8010 (trade name, manufactured by Shin-Etsu Silicone), 50 parts by mass of tetrahydrofuran, and 50 parts by mass of N-methylpyrrolidone, 23 parts by mass of 4,4'-diphenylmethane diisocyanate was added, and a reaction was caused at room temperature for 1 hour. Subsequently, the reaction solution was added to 500 mL of methanol, to generate a white solid. The generated white solid was washed with water, washed with methanol, and dried to obtain Polymer 17.

Synthesis of Polymer 18 Used for Producing Resin Sheet 18

The same procedures as in the synthesis of Polymer 16 were performed except for changes to the compositions of the structure unit (a)-forming monomer and the structure unit (b)-forming monomer described in Table 1 described later, to synthesize Polymer 18.

Synthesis of Polymer 19 Used for Producing Resin Sheet 19

A reaction between 2-methacryloxyethyl isocyanate and ethylamine was caused in accordance with the following formula to obtain 2-(3-propylureido)ethyl methacrylate. The same procedures as in the synthesis of Polymer 1 were performed except for changes to the compositions of the structure unit (a)-forming monomer and the structure unit (b)-forming monomer, to synthesize Polymer 19.

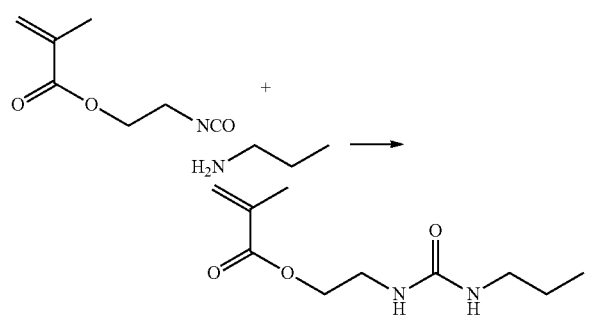

Production of Resin Sheet 1

Polymer 1 (100 parts by mass) and 0.3 parts by mass of PERBUTYL D were mixed together, and subjected to a heat-press treatment (pressure: 10 MPa) at 150° C. for 10 minutes, to produce Resin sheet 1 having a length of 60 mm, a width of 60 mm, and a thickness of 2 mm.

Production of Resin Sheets 2 to 20 and c1 to c3

The same procedures as in Resin sheet 1 were performed except that Polymer 1 was replaced by Polymers 2 to 20 and c1 to c3, and the amount of PERBUTYL D was changed to amounts (parts by mass) in Table 1 described later, to produce Resin sheets 2 to 20 and c1 to c3. Incidentally, in the production of Resin sheets c1 and c3, PERBUTYL D was not used.

Production of Resin Sheets 21 and 22

The same procedures as in Resin sheet 1 were performed except that Polymer 1 was replaced by Polymers 21 and 22, and PERBUTYL D was replaced by additives (c) in Table 1 described later in amounts in Table 1 described later, to produce Resin sheets 21 and 22.

Production of Resin Sheet 23

Polymer 23 was employed and the same heat-press treatment as in Resin sheet 1 was performed, to produce a sheet having a length of 60 mm, a width of 60 mm, and a thickness of 2 mm. This sheet was irradiated with an electron beam at an acceleration voltage of 2 MeV at a dose of 300 kGy, to produce Resin sheet 23.

Production of Resin Sheet 24

Polymer 24 was employed and the same heat-press treatment as in Resin sheet 1 was performed, to produce a sheet having a length of 60 mm, a width of 60 mm, and a thickness of 2 mm. This sheet was irradiated with γ-rays from Co60 serving as the radiation source and at a dose of 300 kGy, to produce Resin sheet 24.

Production of Resin Sheet c4

Vinyl terminated polydimethylsiloxane DMS-V41 (96 parts by mass, trade name, manufactured by Gelest Inc.), 4 parts by mass of methylhydrosiloxane-dimethylsiloxane copolymer HMS-301 (trade name, manufactured by Gelest Inc.), and 0.03 parts by mass of platinum catalyst SIP6830.3 (trade name, manufactured by Gelest Inc.) were mixed together, and thermally cured at 150° C. for 5 minutes, to produce Resin sheet c4 having a length of 60 mm, a width of 60 mm, and a thickness of 2 mm.

Production of Resin Sheet c5

Vinyl terminated polydimethylsiloxane DMS-V41 (67 parts by mass, trade name, manufactured by Gelest Inc.), 3 parts by mass of methylhydrosiloxane-dimethylsiloxane copolymer HMS-301 (trade name, manufactured by Gelest Inc.), 30 parts by mass of fumed silica AEROSIL R974 (trade name, manufactured by NIPPON AEROSIL CO., LTD., average primary particle size: 12 nm, surface-treated with dimethyldichlorosilane), and 0.05 parts by mass of platinum catalyst SIP6830.3 (manufactured by Gelest Inc.) were mixed together, and thermally cured at 150° C. for 5 minutes, to produce Resin sheet c5 having a length of 60 mm, a width of 60 mm, and a thickness of 2 mm.

Polymers (A) constituting Resin sheets 1 to 24 produced above and the polymers constituting Resin sheets c1 to c5 produced above were measured in terms of gel fraction and density in the following manner. The results are described later in Table 1.

Gel Fraction

A sample (1 g) cut out from each resin sheet was immersed in 10 g of tetrahydrofuran at 25° C. for 24 hours, and subsequently the sample was taken out and dried at 100° C. for 2 hours. From the mass $m_0$ of the sample before the immersion and the mass $m_{24}$ of the sample after the immersion and drying, gel fraction was calculated by the following formula.

Gel fraction(mass %)=$(m_{24}/m_0) \times 100$

Density

Each resin sheet obtained and having a thickness of 2 mm was measured in terms of density at 25° C. in accordance with a density determination method of method A (water displacement method) described in JIS K7112 (1999), using an electronic densimeter (manufactured by Alfa Mirage Co., Ltd., trade name: "SD-200L").

TABLE 1

| No. | Moiety (a)-forming monomer Species | Amount | Moiety (b)-forming monomer Species | Amount | Moiety (b)-forming monomer Species | Amount | Mass-average molecular weight (×10⁴) | Additive (c) Species | Amount | Gel fraction (mass %) |
|---|---|---|---|---|---|---|---|---|---|---|
| 1 | KF-2012 | 50 | Styrene | 50 | — | — | 6.0 | PERBUTYL D | 0.3 | 62 |
| 2 | KF-2012 | 50 | Styrene | 50 | — | — | | PERBUTYL D | 0.5 | 71 |
| 3 | KF-2012 | 50 | Styrene | 50 | — | — | | PERBUTYL D | 1 | 80 |
| 4 | KF-2012 | 50 | Styrene | 50 | — | — | | PERBUTYL D | 3 | 85 |
| 5 | KF-2012 | 50 | Methyl methacrylate | 50 | — | — | 5.6 | PERBUTYL D | 3 | 83 |
| 6 | KF-2012 | 50 | Styrene 2,2,2-Trifluoroethyl methacrylate | 20 30 | — | — | 5.8 | PERBUTYL D | 3 | 88 |
| 7 | KF-2012 | 50 | Methyl methacrylate 2,2,2-Trifluoroethyl methacrylate | 20 30 | — | — | 6.1 | PERBUTYL D | 3 | 90 |
| 8 | KF-2012 | 50 | Styrene 2,2,3,3,3-Pentafluoropropyl methacrylate | 20 30 | — | — | 6.2 | PERBUTYL D | 3 | 93 |
| 9 | KF-2012 | 50 | Styrene 1H,1H,2H,2H-nonafluorohexyl methacrylate | 20 30 | — | — | 6.5 | PERBUTYL D | 3 | 90 |
| 10 | KF-2012 | 50 | Styrene Methyl α-trifluoromethylmethacrylate | 20 30 | — | — | 5.5 | PERBUTYL D | 3 | 88 |
| 11 | KF-2012 | 50 | Styrene 1,1,1,3,3,3-Hexafluoroisopropyl methacrylate | 20 30 | — | — | 7.8 | PERBUTYL D | 3 | 92 |
| 12 | KF-2012 | 50 | Styrene Pentafluorostyrene | 20 30 | — | — | 6.1 | PERBUTYL D | 3 | 93 |
| 13 | VPS-1001 | 50 | Styrene Pentafluorostyrene | 20 30 | — | — | 5.9 | PERBUTYL D | 3 | 92 |
| 14 | KF-2012 | 50 | Dimethylmethacrylamide Pentafluorostyrene | 20 30 | — | — | 6.4 | PERBUTYL D | 3 | 91 |
| 15 | KF-2012 | 50 | Dimethylmethacrylamide 2,2,2-Trifluoroethyl methacrylate | 20 30 | — | — | 5.5 | PERBUTYL D | 3 | 90 |
| 16 | KF-6000 | 79 | 4,4'-diphenylmethane diisocyanate | 21 | — | — | 8.5 | PERBUTYL D | 3 | 93 |
| 17 | KF-8010 | 77 | 4,4'-diphenylmethane diisocyanate | 23 | — | — | 9.0 | PERBUTYL D | 3 | 95 |
| 18 | KF-8010 | 84 | Hexamethylene diisocyanate | 16 | — | — | 8.2 | PERBUTYL D | 3 | 93 |
| 19 | KF-2012 | 84 | 2-(3-Propylureido)ethyl methacrylate | 16 | — | — | 6.5 | PERBUTYL D | 3 | 90 |
| 20 | KF-2012 | 50 | Styrene Pentafluorostyrene | 17 30 | Allyl methacrylate | 3 | 5.9 | PERBUTYL D | 3 | 96 |
| 21 | KF-2012 | 50 | Styrene Pentafluorostyrene | 17 30 | Glycidyl methacrylate | 3 | 6.5 | Benzyl(4-hydroxyphenyl)methylsulfonium hexafluoroantimonate | 3 | 85 |
| 22 | KF-2012 | 50 | Styrene Pentafluorostyrene | 17 30 | Glycidyl methacrylate | 3 | 5.9 | Diaminopropane | 3 | 90 |
| 23 | KF-2012 | 50 | Styrene Pentafluorostyrene | 20 30 | — | — | 6.2 | Electron Beam | — | 92 |
| 24 | KF-2012 | 50 | Styrene Pentafluorostyrene | 20 30 | — | — | 6.2 | γ-Rays | — | 92 |
| c1 | KF-2012 | 50 | Styrene | 50 | — | — | 6.0 | — | — | 0 |
| c2 | KF-2012 | 50 | Styrene | 50 | — | — | 6.0 | PERBUTYL D | 0.2 | 40 |
| c3 | KF-2012 | 50 | Styrene Pentafluorostyrene | 20 30 | — | — | 6.2 | — | — | 0 |
| c4 | Crosslinked polysiloxane | 100 | — | — | — | — | — | — | — | 98 |
| c5 | Crosslinked polysiloxane | 70 | — | — | — | — | — | Silica | 30 | 98 |

Notes for Table 1

KF-2012: trade name, single-end methacryl-modified silicone manufactured by Shin-Etsu Silicone, mass-average molecular weight: 4,600

VPS-1001: trade name, polydimethylsiloxane unit-containing polymeric azo polymerization initiator manufactured by Wako Pure Chemical Industries, Ltd., mass-average molecular weight of polysiloxane unit: 10,000

KF-6000: trade name, dual-end hydroxy-modified silicone oil manufactured by Shin-Etsu Silicone, mass-average molecular weight: 940

KF-8010: trade name, dual-end amino-modified silicone oil manufactured by Shin-Etsu Silicone, mass-average molecular weight: 860

PERBUTYL D: trade name, organic peroxide manufactured by NOF CORPORATION

"Amount" are based on parts by mass.

Resin sheets 1 to 24 and c1 to c5 produced above were tested for acoustic characteristics and mechanical strength in the following manner. The results are described later in Table 2.

Acoustic Wave (Ultrasonic Wave) Sensitivity

Sine wave signals (single wave) at 10 MHz outputted from an ultrasonic wave generator (manufactured by IWATSU TEST INSTRUMENTS CORPORATION, function generator, trade name: "FG-350") were inputted into an ultrasonic wave probe (manufactured by Japan Probe Co, Ltd.), to generate, from the ultrasonic wave probe, ultrasonic pulse waves having a center frequency of 10 MHz in water. The amplitudes of the generated ultrasonic waves before and after passing through such an obtained resin sheet having a thickness of 2 mm were measured using an ultrasonic wave receiver (manufactured by Matsushita Electric Industrial Co., oscilloscope, trade name: "VP-5204A") in an environment at a water temperature of 25° C. Such acoustic wave (ultrasonic wave) sensitivities were compared, to thereby compare acoustic wave (ultrasonic wave) attenuations of the materials.

Incidentally, the acoustic wave (ultrasonic wave) sensitivity is a numerical value provided by a formula below.

In the following formula, Vin represents the voltage peak value of an inputted wave generated by the ultrasonic wave generator and having a half width of 50 nsec or less. Vs represents a voltage value obtained at the time when the generated acoustic waves (ultrasonic waves) pass the sheet, and acoustic waves (ultrasonic waves) reflected by a surface facing the sheet are received by the ultrasonic wave generator. The higher the acoustic wave (ultrasonic wave) sensitivity, the lower the acoustic wave (ultrasonic wave) attenuation.

$$\text{Acoustic wave(ultrasonic wave)sensitivity} = 20 \times \text{Log}(Vs/Vin)$$

The following grading system was used for evaluation of the acoustic wave (ultrasonic wave) sensitivity. In this test, "C" and better grades are pass grades.

Grading System
 A: −66 dB or more
 B: −68 dB or more and less than −66 dB
 C: −70 dB or more and less than −68 dB
 D: −72 dB or more and less than −70 dB
 E: less than −72 dB Acoustic Impedance Such an obtained resin sheet having a thickness of 2 mm was measured in terms of density at 25° C. in accordance with a density determination method of method A (water displacement method) described in JIS K7112 (1999), using an electronic densimeter (manufactured by Alfa Mirage Co., Ltd., trade name "SD-200L"). The acoustic velocity of ultrasonic waves was measured at 25° C. in accordance with JIS Z2353 (2003), using a sing-around acoustic velocity measurement apparatus (manufactured by ULTRASONIC ENGINEERING CO., LTD., trade name: "UVM-2"). The measured density was multiplied by the measured acoustic velocity to determine acoustic impedance. The following grading system was used for evaluation of the acoustic impedance. In this test, "C" and better grades are pass grades.

Grading System
 A: $1.30 \times 10^6$ kg/m²/s or more and less than $1.70 \times 10^6$ kg/m²/s
 B: $1.20 \times 10^6$ kg/m²/s or more and less than $1.30 \times 10^6$ kg/m²/s
 C: $1.10 \times 10^6$ kg/m²/s or more and less than $1.20 \times 10^6$ kg/m²/s
 D: less than $1.10 \times 10^6$ kg/m²/s Hardness Such an obtained silicone resin sheet having a thickness of 2 mm was measured in accordance with JIS K6253-3 (2012), for type A durometer hardness, using a rubber hardness tester (manufactured by EXCEL INC., trade name "RH-201A"). "C" and better grades are pass grades.

Grading System
 A: 40° or more
 B: 30° or more and less than 40°
 C: 20° or more and less than 30°
 D: 10° or more and less than 20°
 E: 5° or more and less than 10°
 F: less than 5°

Tear Strength Test

From such an obtained resin sheet having a thickness of 2 mm, a trouser-shaped test piece was prepared in accordance with JIS K6252 (2007), and measured in terms of tear strength. The tear strength was evaluated in accordance with the following grading system. In this test, "D" and better grades are pass grades.

Grading System
 A: 10 N/cm or more
 B: 5 N/cm or more and less than 10 N/cm
 C: 1 N/cm or more and less than 5 N/cm
 D: 0.5 N/cm or more and less than 1 N/cm
 E: 0.1 N/cm or more and less than 0.5 N/cm
 F: less than 0.1 N/cm

TABLE 2

Table 2

| Resin sheet No. | Density (g/cm³) | Acoustic characteristics | | Mechanical strength | |
|---|---|---|---|---|---|
| | | Acoustic wave (ultrasonic wave) sensitivity | Acoustic impedance | Hardness | Tear strength |
| 1 | 1.05 | B | C | A | C |
| 2 | 1.05 | B | C | A | C |
| 3 | 1.05 | B | C | A | B |
| 4 | 1.05 | B | C | A | A |
| 5 | 1.06 | B | C | B | B |
| 6 | 1.08 | A | B | A | A |
| 7 | 1.09 | B | B | B | B |
| 8 | 1.13 | A | A | A | A |
| 9 | 1.14 | A | A | A | A |
| 10 | 1.08 | A | B | A | A |
| 11 | 1.14 | A | A | A | A |
| 12 | 1.12 | A | A | A | A |
| 13 | 1.12 | B | A | A | A |
| 14 | 1.12 | C | A | A | A |
| 15 | 1.13 | C | B | B | B |
| 16 | 1.03 | B | C | C | A |
| 17 | 1.04 | B | C | C | A |
| 18 | 1.03 | B | C | C | B |
| 19 | 1.03 | A | C | C | A |
| 20 | 1.12 | A | A | A | A |
| 21 | 1.12 | A | A | A | B |
| 22 | 1.12 | A | A | A | B |
| 23 | 1.12 | A | A | A | A |
| 24 | 1.12 | A | A | A | A |
| c1 | 1.05 | B | C | A | F |
| c2 | 1.05 | B | C | A | F |
| c3 | 1.12 | A | A | A | F |
| c4 | 0.98 | A | D | F | F |
| c5 | 1.12 | E | B | B | B |

As is clear from Table 2, resin sheets of Resin sheets c1 to c4 composed of resin materials that do not fall within the scope of the present invention were found to have very poor tear strengths. Resin sheet c5 composed of a resin material that does not fall within the scope of the present invention and contains filler was found to have a very poor acoustic wave sensitivity.

By contrast, Resin sheets 1 to 24 composed of resin materials according to the present invention were found to have sufficient acoustic characteristics and high tear strengths.

The present invention has been described together with embodiments thereof. However, we do not intend to limit our invention in any details of the descriptions unless otherwise specified, and we believe that our invention should be broadly constructed without departing from the spirit and scope of the invention described in the attached claims.

1 acoustic lens
2 acoustic matching layer
3 piezoelectric element layer
4 backing member
7 case
9 cord
10 ultrasound probe (probe)

What is claimed is:

1. An acoustic wave probe comprising an acoustic lens which comprises an acoustic-wave-probe resin material comprising a polymer that includes (a) a moiety having a polysiloxane bond, and (b) a moiety having at least one of an ester bond, an amide bond, a urethane bond, a urea bond, or an aromatic-ring-vinyl-derived structure, and that has a gel fraction of 60 mass % or more.

2. The acoustic wave probe according to claim 1, wherein the polymer has, in a side chain, any one of an ester bond, an amide bond, a urethane bond, a urea bond, and an aromatic ring.

3. The acoustic wave probe according to claim 1, wherein, in the polymer, at least a portion of the moiety (b) is (b1) an acryloyloxy structure unit, (b2) an acrylamide structure unit, or (b3) a styrene structure unit.

4. The acoustic wave probe according to claim 3, wherein the moiety (a) is represented by Formula (1) below, the acryloyloxy structure unit (b1) is represented by Formula (2) below, the acrylamide structure unit (b2) is represented by Formula (3) below, and the styrene structure unit (b3) is represented by Formula (4) below,

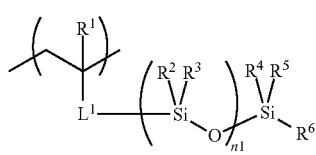

Formula (1)

where $R^1$ to $R^6$ each independently represent a hydrogen atom or a monovalent organic group, $L^1$ represents a divalent linking group, and n1 represents an integer of 3 to 10,000,

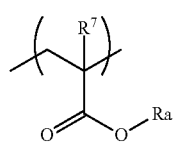

Formula (2)

where $R^7$ and Ra each independently represent a hydrogen atom or a monovalent organic group,

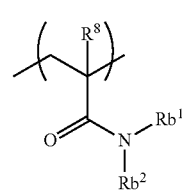

Formula (3)

where $R^8$, $Rb^1$, and $Rb^2$ each independently represent a hydrogen atom or a monovalent organic group, and

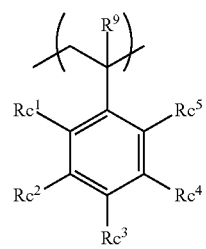

Formula (4)

where $R^9$ and $Rc^1$ to $Rc^5$ each independently represent a hydrogen atom, a halogen atom, or a monovalent organic group.

5. The acoustic wave probe according to claim 1, wherein, in the polymer, at least a portion of the moiety (b) has at least one of an ester bond or an aromatic-ring-vinyl-derived structure.

6. The acoustic wave probe according to claim 1, wherein the polymer contains a fluorine atom.

7. The acoustic wave probe according to claim 1, wherein the moiety (b) has 5 or more fluorine atoms.

8. An acoustic wave determination device comprising the acoustic wave probe according to claim 1.

9. An ultrasound diagnostic apparatus comprising the acoustic wave probe according to claim 1.

10. A photo-acoustic wave determination device comprising an acoustic lens which comprises an acoustic-wave-probe resin material comprising a polymer that includes (a) a moiety having a polysiloxane bond, and (b) a moiety having at least one of an ester bond, an amide bond, a urethane bond, a urea bond, or an aromatic-ring-vinyl-derived structure, and that has a gel fraction of 60 mass % or more.

11. An ultrasonic endoscope comprising an acoustic lens which comprises an acoustic-wave-probe resin material comprising a polymer that includes (a) a moiety having a polysiloxane bond, and (b) a moiety having at least one of an ester bond, an amide bond, a urethane bond, a urea bond, or an aromatic-ring-vinyl-derived structure, and that has a gel fraction of 60 mass % or more.

* * * * *